United States Patent
Karesh

(10) Patent No.: US 11,698,231 B2
(45) Date of Patent: *Jul. 11, 2023

(54) TUNABLE WICKING STRUCTURES AND A SYSTEM FOR A WICKING STRUCTURE

(71) Applicant: General Electric Company, Schenectady, NY (US)

(72) Inventor: Matthew Karesh, Liberty Township, OH (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/525,537

(22) Filed: Nov. 12, 2021

(65) Prior Publication Data
US 2022/0136781 A1 May 5, 2022

Related U.S. Application Data

(63) Continuation of application No. 16/228,281, filed on Dec. 20, 2018, now Pat. No. 11,187,469.

(51) Int. Cl.
| | |
|---|---|
| *F28D 15/04* | (2006.01) |
| *A61M 16/18* | (2006.01) |
| *F28D 15/02* | (2006.01) |
| *B22F 10/28* | (2021.01) |
| *B22F 10/80* | (2021.01) |

(52) U.S. Cl.
CPC ........... *F28D 15/046* (2013.01); *A61M 16/18* (2013.01); *F28D 15/0233* (2013.01); *B22F 10/28* (2021.01); *B22F 10/80* (2021.01)

(58) Field of Classification Search
CPC ........ F28D 15/046; F28D 15/04; F28D 15/00; A61M 16/18; A61M 16/00; A61M 16/80; A61L 9/127; A61L 9/037; B01F 3/04085
USPC ......... 128/204.13; 165/80.4, 104.21, 104.26, 165/104.33
See application file for complete search history.

(56) References Cited

U.S. PATENT DOCUMENTS

| | | | | |
|---|---|---|---|---|
| 3,651,805 | A * | 3/1972 | Breiling ................ | A61M 16/18 128/203.14 |
| 4,075,297 | A * | 2/1978 | Seidel .................. | A61M 16/18 261/DIG. 65 |
| 4,274,479 | A * | 6/1981 | Eastman ............... | F28D 15/046 29/890.032 |
| 4,286,754 | A * | 9/1981 | Jones .................. | A01M 1/2044 239/6 |
| 6,293,333 | B1 * | 9/2001 | Ponnappan ......... | F28D 15/0233 29/890.032 |
| 10,722,677 | B2 * | 7/2020 | Heidschmidt ......... | A61M 16/18 |

(Continued)

*Primary Examiner* — Justine R Yu
*Assistant Examiner* — Kelsey E Baller

(57) ABSTRACT

Various systems and methods are provided for creating a wicking structure. In one example, a method for creating a wicking structure can include creating, using a 3D printing technique, a macro wicking element including a lattice structure formed by a grid of a first material, the lattice structure including pores formed between the grid of first material. The method can also include creating, using the 3D printing technique, a first micro wicking element including powder particles distributed within the pores of the lattice structure, and creating, using the 3D printing technique, a second micro wicking element by removing at least a portion of the lattice structure.

11 Claims, 6 Drawing Sheets

(56) References Cited

U.S. PATENT DOCUMENTS

| | | | | |
|---|---|---|---|---|
| 2004/0159422 A1* | 8/2004 | Zuo | ................ | F28D 20/023 |
| | | | | 257/E23.088 |
| 2007/0034357 A1* | 2/2007 | Hou | ................ | B23P 15/26 |
| | | | | 29/890.032 |
| 2007/0228116 A1* | 10/2007 | Hsu | ................ | B22F 7/064 |
| | | | | 228/244 |
| 2010/0051028 A1* | 3/2010 | Kleinschmidt | ....... | A61M 16/18 |
| | | | | 128/204.13 |
| 2010/0301128 A1* | 12/2010 | Pisklak | ............... | A01M 1/2044 |
| | | | | 239/6 |
| 2020/0309469 A1* | 10/2020 | Maxwell | ............... | F28D 15/046 |

* cited by examiner

TUNABLE WICKING STRUCTURES AND A SYSTEM FOR A WICKING STRUCTURE

CROSS-REFERENCE TO RELATED APPLICATIONS

The present matter is a continuation of and claims priority to U.S. patent application Ser. No. 16/228,281, filed Dec. 20, 2018, and titled "TUNABLE WICKING STRUCTURES AND A SYSTEM FOR A WICKING STRUCTURE," the contents of which are hereby incorporated herein by reference.

FIELD

Embodiments of the subject matter disclosed herein relate to methods and systems for a tunable wicking structure.

BACKGROUND

Wicking structures may be used in a variety of applications in order to control and/or direct a flow of fluid (e.g., via capillary action). For example, wicking structures may be used in candles/lamps (to draw liquid fuel for maintaining a flame), air fresheners (to draw scented oil to a scent distribution area), vaporization devices such as those used for administering anesthesia (to draw liquids to a vaporization surface), air/liquid separators (to draw and direct liquid away from an air/liquid mix), and/or other applications. The capillary action in wicking structures occurs due to the presence of hollow structures (e.g., tubes, pores, cells, etc.) in a wick. Adhesion between a liquid and an inner wall of a hollow structure pulls the liquid up the hollow structure, and thus up the wicking structure.

BRIEF DESCRIPTION

In one embodiment, a tunable wicking structure comprises a macro wicking element including a lattice structure formed by a grid of solid material, the lattice structure including pores formed between the solid material, and a micro wicking element including powder particles distributed within the pores of the lattice structure.

In another embodiment, a tunable wicking structure comprises a micro wicking element comprising a plurality of powder particles, each powder particle of the micro wicking element being partially joined to at least one other powder particle of the micro wicking element, and wherein a plurality of channels are formed between partially joined powder particles of the micro wicking element for drawing liquid through the micro wicking element via capillary action.

In another embodiment, a system comprises a liquid reservoir for a vaporizer of an anesthesia machine, a heating element coupled to a region of the liquid reservoir, and a tunable wick disposed in the region of the liquid reservoir, the wick comprising a micro wicking element including a plurality of powder particles, each powder particle of the micro wicking element being partially joined to at least one other powder particle of the micro wicking element to form a plurality of channels for drawing liquid from the liquid reservoir through the micro wicking element toward the heating element via capillary action, the plurality of channels having a continuously variable size along a dimension of the micro wicking element.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
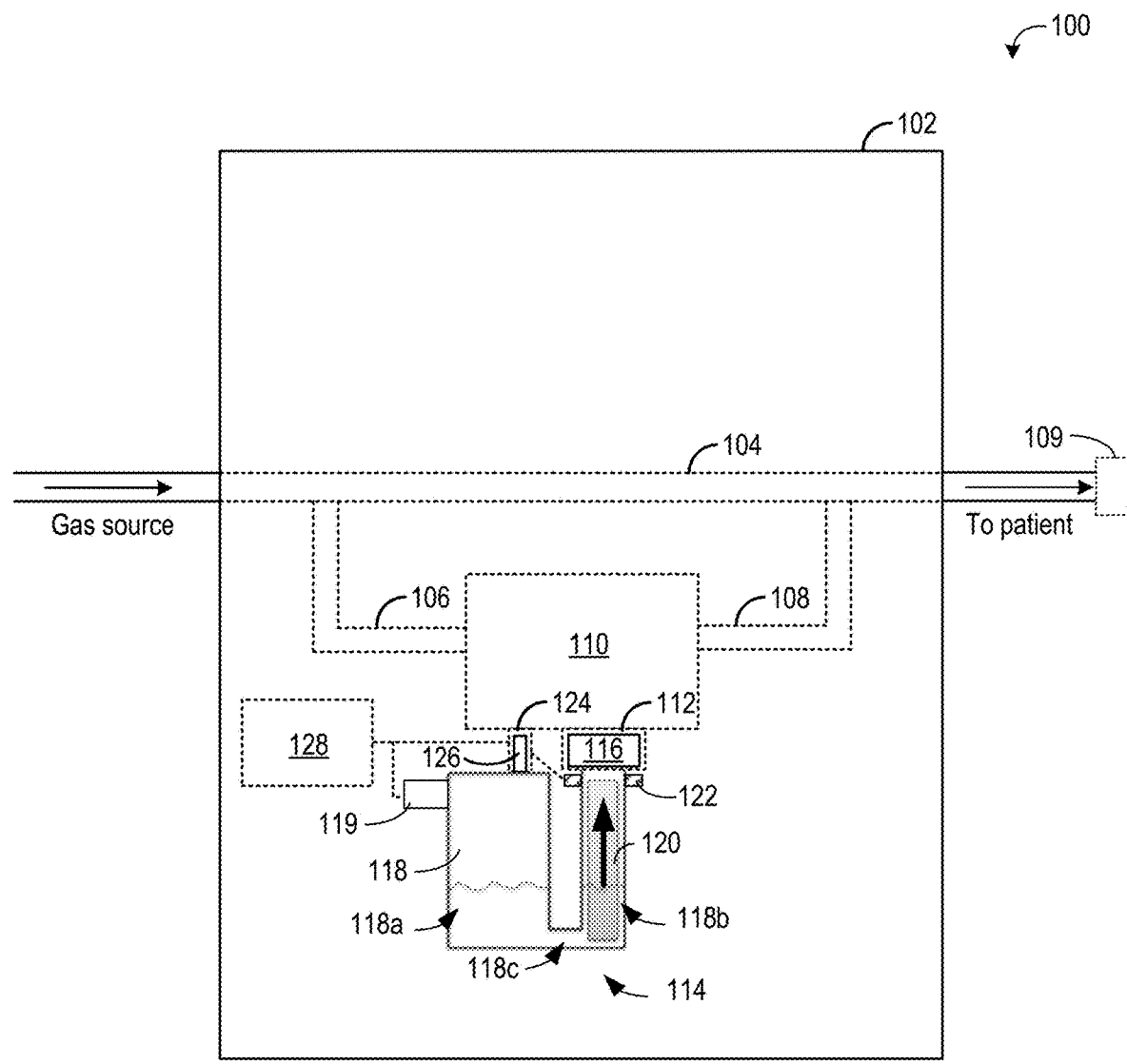
FIG. 1 schematically shows an exemplary embodiment of a patient gas delivery system including a tunable wicking structure.
Figure 2:
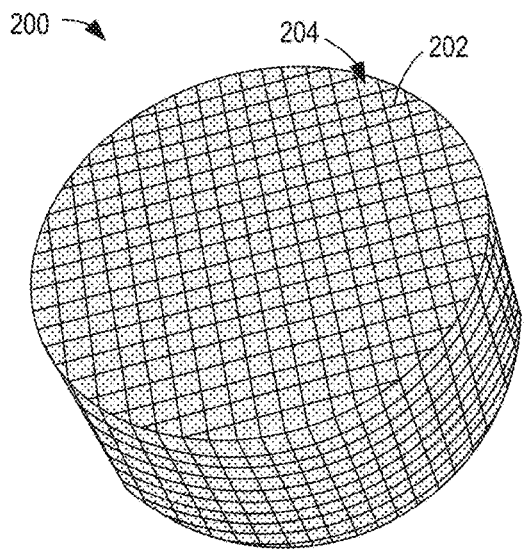
FIG. 2 shows an exemplary embodiment of a tunable wicking structure.
Figure 3:
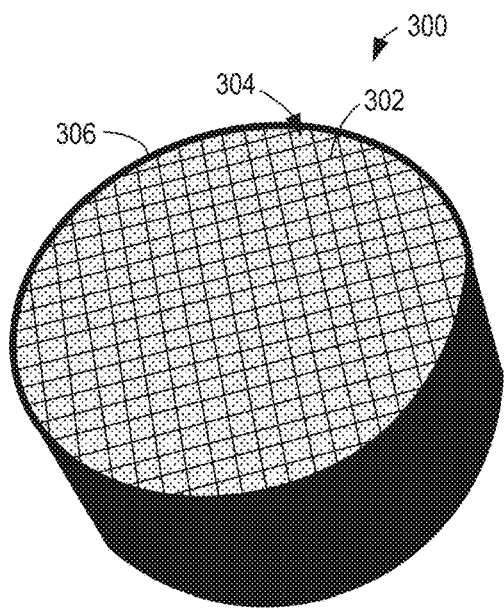
FIG. 3 shows an exemplary embodiment of a tunable wicking structure including an encapsulating structure.
Figure 4:
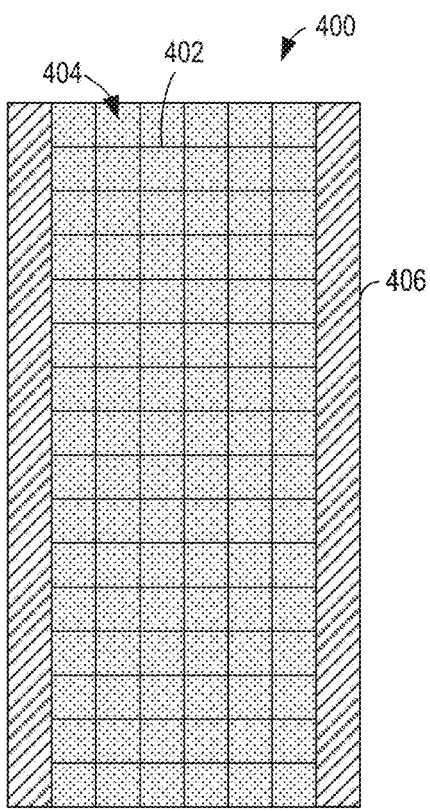
FIGS. 4 and 5 show cross-sectional views of exemplary embodiments of tunable wicking structures having different configurations.
Figure 5:
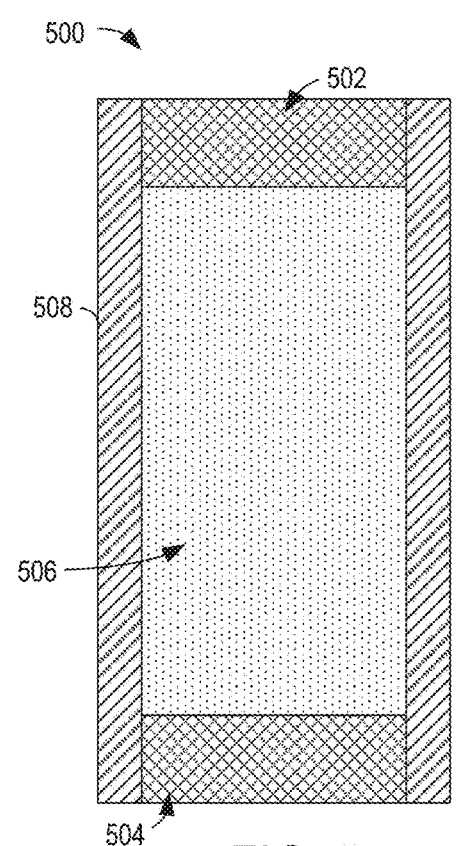

The following description relates to various embodiments of a tunable wicking structure, such as the tunable wicking structure shown in FIGS. 1-9. The tunable wicking structure may be included in a variety of environments, including the patient gas delivery system of FIG. 1, the heat pipe of FIG. 8, and the air/liquid separator of FIG. 9. An example of a tunable wicking structure is depicted in FIG. 2, showing components of the tunable wicking structure including a lattice macro structure and powder particles forming a micro structure within pores of the lattice. An example of a tunable wicking structure that includes an encapsulation structure is depicted in FIG. 3. Examples of different configurations that may be used to form a tunable wicking structure are depicted in FIGS. 4 and 5. FIGS. 6 and 7 show detail, microscopic views of powder particle arrangements within a tunable wicking structure. An example of a method for fabricating a tunable wicking structure is shown in FIG. 10, the method including use of additive manufacturing to generate components of the tunable wicking structure.

The tunable wicking structures described herein utilize sintered powder within a larger structure (which may optionally be removed to form a final wicking structure product) to provide wicking capability through capillary action. In this way, the tunable wicking structures may have a "two-phase" structure, including solid and semi-solid powder (e.g., produced using additive manufacturing). The use of sintered powder allows the tunable wicking structures to be integrated into other parts and tuned to a given application of the tunable wicking structure. The tunable wicking structures can be tuned to include different pore sizes within a lattice structure and/or have variable geometry, unlike other wicks, which may be limited to basic shapes and have a single pore size.

For example, the tunable wicking structures may include tunable macro structures having various lattice size, shape, and/or orientation, through which part strength, thermal properties, mass, density, damping characteristics, and/or other parameters of the wicking structure may be configured for an associated usage environment of the tunable wicking structures. The macro structures may be uniform or non-uniform throughout the body of the wicking structure. The macrostructures may be present throughout the entire body of the wicking structure, intermittently present throughout the body of the wicking structure, and/or omitted entirely from the body of the wicking structure (e.g., leaving only sintered powder forming a micro wicking structure). The above-described parameters of the macro structures may be tuned to fit a size/shape of an environment in which the tunable wicking structure is positioned and/or to provide a targeted capillary wicking capability for the tunable wicking structure and/or for different regions of the tunable wicking structure.

The tunable wicking structures may also include tunable micro wicking structures having various sinter powder distribution, density, size, sintering characteristics, and/or other parameters. The powder may be sintered within electron beam melting (EBM) via a hard sinter parameter, and the parameter set used for manufacturing the micro wicking structures may be uniform through the body of the wicking structure or vary to provide different structures throughout the body of the wicking structure. The powder may be sintered via post build heat treatment (e.g., performed after manufacturing the body of the wicking structure). The powder may be light sintered using EBM and encapsulated via a macro structure, a secondary wick (e.g., formed of ceramic, metal, plastic, and/or other materials) joined to an additive structure associated with the powder, a membrane, and/or a secondary additive melt operation (e.g., targeting an external region of the micro wicking structure/external facing powder particles of the wicking structure and/or additional material that is fully melted around the external region of the micro wicking structure). For example, a membrane may be joined with or used to encapsulate the micro wicking structure to allow for selective filtering/wicking of certain fluids (e.g., using reverse osmosis membranes and/or semi-permeable membranes).

The tunable wicking structures described herein enable graded or variable capillary pumping along a direction, which can achieve improved pumping action from a bottom of a sump, where the wicking structure may provide a higher capillary wicking capability (e.g., via smaller channels or other parameter adjustments relative to other regions of the wicking structure) in regions where a liquid level is relatively low. Similarly, the wicking structure may be configured to promote uniform radial flow by tuning capillary wicking capability in a radial direction. Tunable geometry in the wicking structures also enables for pumping over larger distances (e.g., by varying the capillary wicking capability along a length of the wicking structure). The use of additive manufacturing to build the wicking structure (e.g., as described with respect to FIG. 10) allows for a continuous change in porosity along a direction of the wicking structure, thereby increasing manufacturing efficiency relative to structures constructed using multi-step sintering and part joining and providing opportunities for constructing complex wicking structure configurations that are not able to be manufactured using other mechanisms.

FIG. 1 schematically shows an exemplary embodiment of an environment for a tunable wicking structure according to the present disclosure: a patient gas delivery system 100 in the form of an anesthesia machine 102. Anesthesia machine may include a gas passage 104. Gas passage 104 may receive fresh gas from a gas source. Fresh gas in the anesthesia machine may split into bypass gas and carrier gas, where the bypass gas flows along gas passage 104 to an outlet of the anesthesia machine. The carrier gas flows into inflow passage 106 and outflow passage 108, where it rejoins with the bypass gas, where the bypass gas and carrier gas are ultimately supplied to a patient (e.g., via a ventilator mechanism 109). The carrier gas may pick up vaporized anesthetic agent in a vapor reservoir 110. In this way, the gas supplied to the patient may be a mix of bypass gas and carrier gas that includes vaporized anesthetic agent.

Vapor reservoir 110 may be configured to house vaporized anesthetic agent received via a port 112 of the vapor reservoir. Port 112 may couple to a liquid anesthetic agent vaporizer unit 114 via a coupling end 116 of the vaporizer unit 114. The vaporizer unit 114 includes a liquid reservoir 118 that stores liquid anesthetic agent (e.g., desflurane, isoflurane, sevoflurane, etc.). The anesthetic agent may be pumped into the liquid reservoir 118 via pump 119 (e.g., which may be coupled to a supply of the liquid anesthetic agent, such as a removable/refillable tank of anesthetic agent that is inserted into the anesthesia machine). An interior of the liquid reservoir may include a first region 118a that is fluidically coupled to a second region 118b via a passageway 118c. In some examples, the first region 118a may include a port or other access region to allow liquid anesthetic agent to be added to the reservoir. The second region 118b includes a tunable wick 120 that is configured to pull liquid from the reservoir upward toward the port 112 (e.g., via capillary action). In some examples, the second region 118b may be sized based on a diameter or width of the tunable wick (e.g., having a diameter and/or width that is less than 5% larger than the diameter and/or width of the wick), and may be smaller in diameter and/or width relative to the first region 118a.

The vaporizer may include and/or be coupled to a heating element shown schematically at 122. Although positioned externally to a top of the second region 118b of the reservoir, it is to be understood that the heating element 122 may be in any suitable location for heating liquid pulled up by the tunable wick 120 in order to produce vaporized anesthetic agent to vapor reservoir 110. For example, the heating element 122 may additionally or alternatively be positioned in and/or around port 112, coupled directly to tunable wick 120, and/or otherwise positioned to vaporize liquid pulled up by tunable wick 120. The vaporizer and/or heating element 122 may be supplied power from anesthesia machine via an electrical connection between a first electrical connector 124 of the anesthesia machine and a second electrical connector 126 of vaporizer unit 114. The power supply to the vaporizer may be modulated via a controller 128 of the anesthesia machine. The controller 128 may control a heating supplied by the heating element 122, which may in turn control an amount of vaporization of the anesthetic agent in order to adjust dosage of the anesthetic agent. The controller 128 may further control operation of the pump 119 in order to adjust an amount of liquid anesthetic agent stored in the reservoir 118.

FIG. 2 shows an exemplary embodiment of a tunable wicking structure 200 useable to provide wicking capability through capillary action. In one embodiment, tunable wicking structure 200 may be used as tunable wick 120 of FIG. 1. Tunable wicking structure 200 includes a macro lattice structure 202, which forms a three-dimensional (3D) grid or matrix of parallel and/or intersecting lines of material. The spacing between the lines of material forms a plurality of pores 204 that create a macro wicking structure (e.g., where the pores serve as pathways for drawing liquid via capillary action). The material of the macro lattice may be uniform in size, shape, spacing, and/or distribution throughout the entire structure or may be nonuniform in size, shape, spacing, and/or distribution throughout the entire structure. As used herein, the term "grid" or "matrix" may be understood to include a structure of solid lines of material that are uniform or non-uniform in size, uniform or nonuniform in shape, uniform or non-uniform in spacing, and/or uniform or non-uniform in distribution throughout the structure.

In some examples, the lines of material forming the grid of the lattice structure may be equally spaced, thereby providing a uniform macro structure of pores. In other examples, the lines of material forming the grid of the lattice structure may be non-equally spaced, thereby providing a non-uniform macro structure of pores (e.g., which may be tuned for an environment in which the wicking structure is used and a targeted capillary action for different regions of the wicking structure based on the environment).

The pores 204 are filled with sintered powder (represented by the dotted pattern within the pores 204) to form a micro pore wicking structure within the macro lattice structure (e.g., where the spacing between surfaces of the powder particles in the pores serve as micro pathways for drawing liquid via capillary action). In this way, the tunable wicking structure 200 provides a two-phase structure using solid and semi-solid powder. The tunable wicking structure 200 may be formed using additive manufacturing, such as electron beam melting (EBM). For example, the lattice structure may be formed by completely melting powder particles to form the lines of material of the lattice, whereas the micro pore wicking structure may be formed by only partially melting/sintering powder particles, such that only a portion of the surface of a given powder particle is joined to a surface of an adjacent powder particle, creating a space between regions of the joined powder particles.

The use of additive manufacturing to form a wicking structure allows for flexible tuning of different parameters of the structure. For example, parameters such as part strength, thermal properties, mass, density, and damping characteristics, among other parameters, may be tuned via lattice size, shape, and/or orientation. The wicking structure may be further tuned via sinter powder distribution. For example, sinter powder may be distributed uniformly throughout each pore of the lattice structure, or non-uniformly (e.g., providing smaller capillaries in certain regions of the wicking structure relative to other regions). In some examples, a porosity of the wicking structure (e.g., a size of the pores of the lattice structure and/or a size of channels formed between powder particles of the micro pore wicking structure) may be continuously variable along at least one dimension of the wicking structure (e.g., along a length of the wicking structure, around a circumference of the wicking structure, etc.) and may be achieved in one or more ways including variable sintering parameters within or outside of the additive manufacturing process.

FIG. 3 shows another exemplary embodiment of a tunable wicking structure 300. Tunable wicking structure 300 may be similar to wicking structure 200 of FIG. 2, and may include a macro lattice structure 302 (analogous to macro lattice structure 202 of FIG. 2) that forms pores 304 (analogous to pores 204 of FIG. 2) that are filled with sintered powder (represented by the dotted pattern within the pores 304). Tunable wicking structure 300 may further be at least partially encapsulated by encapsulation structure 306. In the illustrated example, encapsulation structure 306 comprises a solid structure enclosing and encircling a circumference of the overall cylindrical macro lattice structure 302. The encapsulation structure 306 may be formed of the same material or material composition as the macro lattice structure 302 and/or the powder filling pores of the lattice structure in some examples. In other examples, the encapsulation structure 306 may be formed of a different material or material composition from the macro lattice structure 302 and/or the powder filling pores of the lattice structure. The material used for the encapsulation structure 306 may depend on an environment of the tunable wicking structure 300 (e.g., having heat transfer properties, durability properties, elastomeric properties, weight properties, and/or other parameters selected for the environment and/or use of the wicking structure).

FIG. 4 shows a cross-sectional view of an exemplary embodiment of a tunable wicking structure 400. For example, tunable wicking structure 400 may be shown as a cross-sectional view of a portion of tunable wicking structure 300 of FIG. 3. Tunable wicking structure 400 includes a lattice structure 402 forming pores 404 that are filled with powder as described above with respect to lattice structure 302 and pores 304 of FIG. 3. An encapsulation structure 406 is provided around the lattice structure 402 and may be analogous to encapsulation structure 306 of FIG. 3.

As described above, various parameters of a wicking structure according to the present disclosure may be tuned for different usage environments. An example alternative configuration of a tunable wicking structure is shown in FIG. 5. In contrast to the tunable wicking structure of FIG. 4, which illustrates an exemplary embodiment having lattice structure components extending the entire length/height of the wicking structure and the entire width between interior surfaces of the encapsulation structure. FIG. 5 illustrates an exemplary embodiment of a tunable wicking structure 500 which includes different sub-structures in different sections of the wicking structure. For example, tunable wicking structure 500 includes a first lattice structure 502 in a top region of the wicking structure. The first lattice structure 502 may be analogous to the lattice structure 402 of FIG. 4 and/or the lattice structure 302 of FIG. 3 and may form a macro wicking structure having pores that are filled with powder to create a micro wicking structure as described above. The first lattice structure 502 forms an uppermost and/or top surface of the wicking structure and extends downward from the uppermost and/or top surface along a height of the wicking structure toward a lowermost and/or bottom surface of the wicking structure. In the illustrated example, the first lattice structure 502 has a height that is less than a third of the overall height of the tunable wicking structure 500 (e.g., the first lattice structure 502 may have a height that is in a range of 10-15% of the overall height of the tunable wicking structure 500).

A second lattice structure 504 is positioned in a bottom region of the tunable wicking structure 500. The description of the configuration of the first lattice structure 502 may also apply to the second lattice structure 504. The second lattice structure 504 forms the lowermost and/or bottom surface of the tunable wicking structure and extends upward from the lowermost and/or bottom surface along the height of the wicking structure toward the uppermost and/or top surface of the wicking structure. In the illustrated example, the second lattice structure 504 has a height that is less than a third of the overall height of the tunable wicking structure 500 (e.g., the second lattice structure 504 may have a height that is in a range of 10-15% of the overall height of the wicking structure 500). In some examples, the configuration of the first lattice structure 502 may be substantially the same as the configuration of the second lattice structure 504. For example, dimensions of the first and second lattice structures (e.g., overall height, overall width/diameter, pore size/lattice spacing, thickness of the lines of material forming the grid pattern of the lattice, etc.), composition of the first and second lattice structures (e.g., material(s) used to form the lattice structures), powder particle distribution/density/size within pores of the lattice, and/or other parameters of the first and second lattice structures may be substantially the same as one another. In other examples, one or more (or all) of the above-described parameters may be different in the first lattice structure relative to the second lattice structure.

An open powder region 506 is sandwiched between the first and second lattice structures of the wicking structure 500. The open powder region may include only powder particles forming a micro wicking structure and does not include a macro lattice structure. In some examples, the open powder region 506 may be formed similarly to the first and second lattice structures, with an additional process of removing the lattice structure such that only the powder particles disposed in the pores of the (removed) lattice structure are present in the open powder region. In the illustrated example, the open powder region 506 extends between a bottom surface of the first lattice structure 502 and a top surface of the second lattice structure 504. The open powder region 506 may extend along more than a third of the overall height of the wicking structure 500 (e.g., the open powder region 506 may have a height that is in a range of 70-80% of the overall height of the wicking structure 500). In some examples, the open powder region 506 may have substantially the same powder particle density, distribution, and/or size/size variation as the powder within the pores of the first lattice structure 502 and/or the second lattice structure 504. In other examples, the open powder region 506 may include a different powder particle density, distribution, and/or size/size variations as the powder within the pores of the first lattice structure 502 and/or the second lattice structure 504. The open powder region 506 may be uniform throughout the entire region (e.g., having substantially the same powder particle density, distribution, and/or size/size variation) in some examples. In other examples, the open powder region 506 may have a non-uniform and/or graduated powder particle density, distribution, and/or size/size variation throughout the region. In an illustrative example, powder particle density may be less dense (e.g., having larger channels between powder particles) in a first portion of the open powder region toward a top of the region and may (e.g., linearly or non-linearly) increase in density in a second portion of the open powder region toward a bottom of the region.

An encapsulation structure 508 is provided around the first lattice structure 502, the second lattice structure 504, and the open powder region 506. The encapsulation structure 508 may be analogous to encapsulation structure 306 of FIG. 3 and/or the encapsulation structure 406 of FIG. 4. An inner surface of the encapsulation structure 508 may be adjacent to and/or in direct contact with each of the first lattice structure 502, the second lattice structure 504, and the open powder region 506. In this way, a width/diameter of each of the first lattice structure 502, the second lattice structure 504, and the open powder region 506 may be defined as extending the width/diameter of an interior region within the encapsulation structure 508 (e.g., with a perimeter of the interior region of the encapsulation structure 508 formed by an interior surface(s) of the encapsulation structure 508). For example, the plurality of powder particles in the open powder region 506 of tunable wicking structure 500 may include a first subset of powder particles and a second subset of powder particles, each powder particle of the first set of powder particles being only partially joined to the respective at least one other powder particle of the micro wicking element and not joined to any other structure, and each powder particle of the second set of powder particles being further partially joined to the encapsulation structure.

The exemplary embodiment of FIG. 5 shows a mixed use of powder particles encased in a macro lattice structure (e.g., first and second lattice structures 502 and 504) and powder particles not encased in a macro lattice structure (e.g., open powder region 506). It is to be understood that other examples of wicking structures may include only an open powder region with no lattice structure (e.g., where the powder particles of the wicking structure are only partially joined to one or more adjacent powder particles and are not joined to any other structural element such as a macro lattice structure). Lattice structures may provide additional durability and contactable surface area relative to open powder regions. Removing the lattice structure (e.g., having a wicking structure that does not include a lattice structure and only includes open powder regions) may increase overall capillary wicking capabilities (e.g., capillary wicking strength and/or capacity). Accordingly, wicking structures utilizing lattice structures may be selected for usage environments in which the added durability of the lattice structures and/or the added surface area of the lattice structures (e.g., for providing heat transfer, such as in embodiments where the wicking structure is directly coupled to a heating element) is useful. Wicking structures utilizing only open powder regions (e.g., with no lattice structure) may be selected for usage environments in which improved capillary action is useful.

Figure 6B:
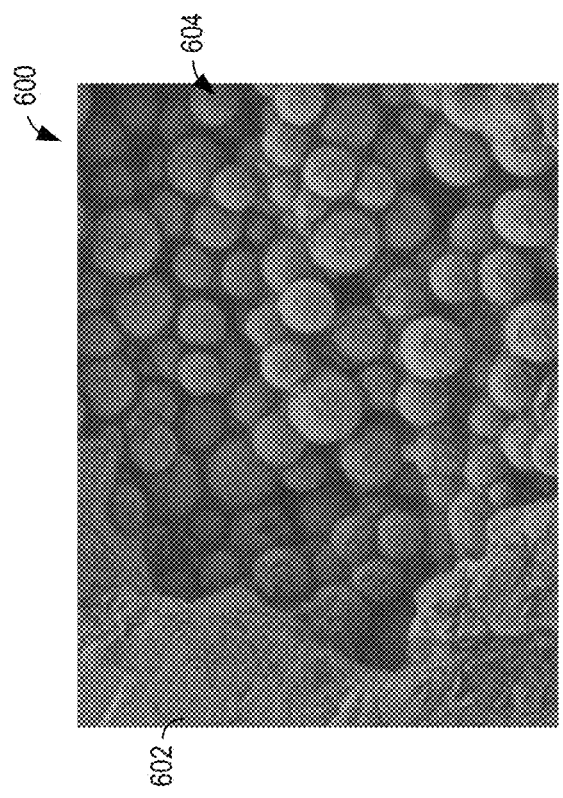
FIGS. 6A-6C show detailed views of an exemplary embodiment of a tunable wicking structure including a lattice at 100× magnification, 250× magnification and 1000× magnification respectively.
Figure 6C:
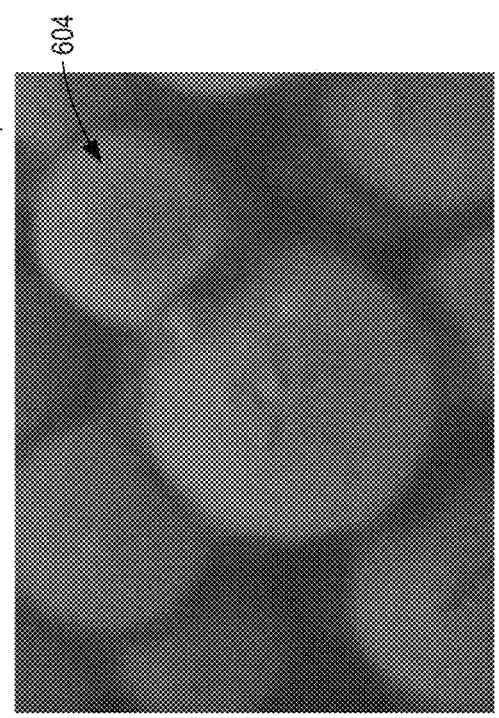
Figure 6A:
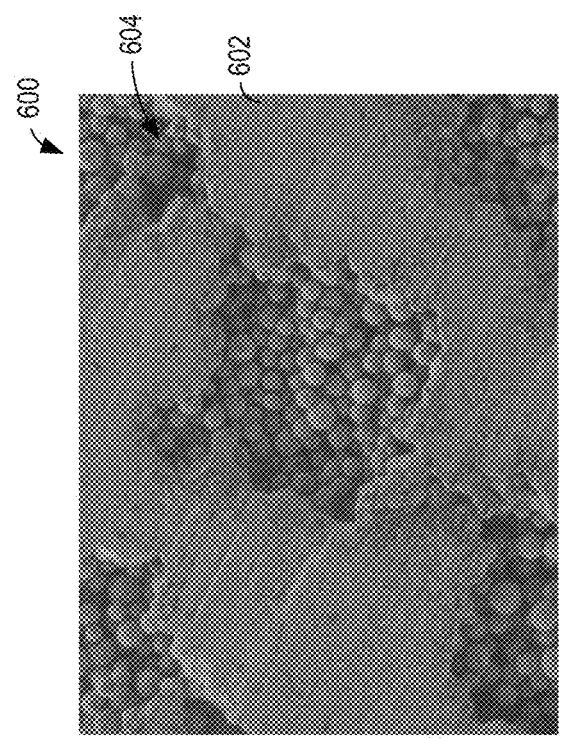

FIGS. 6A-C and 7A-C show detailed, microscopic views of exemplary embodiments of tunable wicking structures, such as the tunable wicking structures 200 and 300 of FIGS. 2 and 3, respectively. FIGS. 6A-C show microscopic views of a tunable wicking structure in which a lattice is maintained for the wicking structure, with powder particles disposed in voids of the lattice to provide micro pores for micro capillary action (e.g., where the voids of the lattice provide macro pores for macro capillary action). For example, the tunable wicking structure illustrated in FIGS. 6A-C may be an example of the powder particles and lattice structure in the tunable wicking structure 400 of FIG. 4 and/or the first lattice structure 502 and/or second lattice structure 504 of the tunable wicking structure 500 of FIG. 5. In FIG. 6A, an exemplary 100× magnification of a portion of a tunable wicking structure 600 is shown, with solid regions of the lattice shown at 602 and powder particles shown at 604. FIG. 6B shows an exemplary 250× magnification of the portion of the tunable wicking structure 600 and FIG. 6C shows an exemplary 1000× magnification of the portion of the tunable wicking structure 600. As most clearly visible in FIG. 6C, the powder particles exhibit necking (e.g., partial bonding with adjacent particles) indicating sintering of the particles.

Figure 7B:
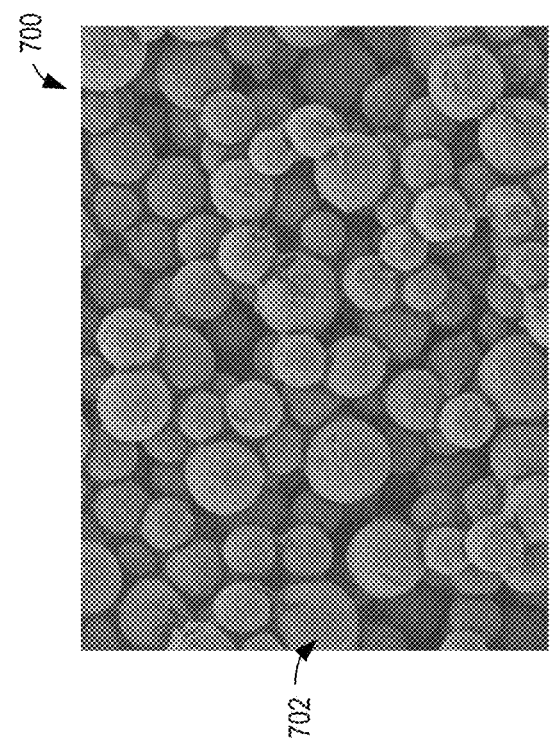
FIGS. 7A-7C show detailed views of an exemplary embodiment of a tunable wicking structure including loose powder particles without a lattice structure at 100× magnification, 250× magnification, and 1000× magnification respectively.
Figure 7C:
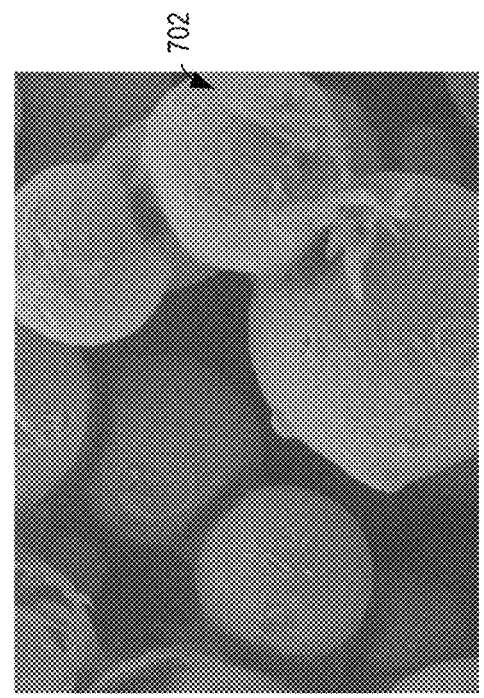
Figure 7A:
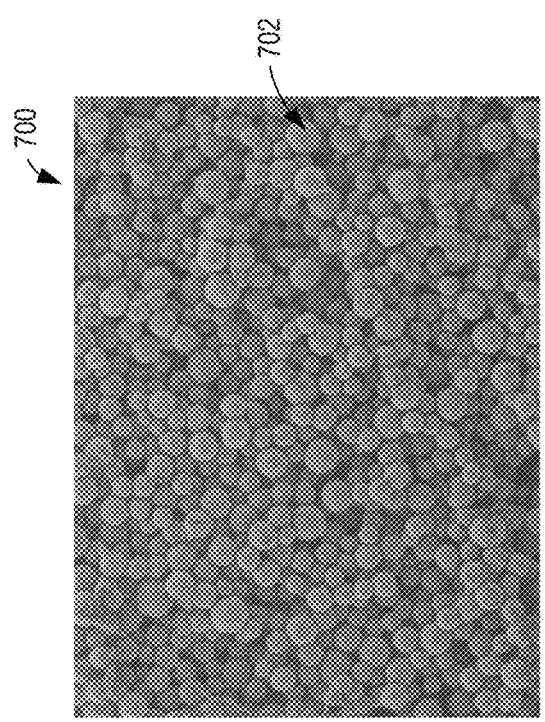

FIGS. 7A-C shows a microscopic view of a tunable wicking structure in which a lattice is removed or not printed for the tunable wicking structure (e.g., wherein the tunable wicking structure is formed of open powder with no macro structure for holding the powder). For example, the tunable wicking structure illustrated in FIGS. 7A-C may be an example of the powder particles in the open powder region 506 of tunable wicking structure 500 of FIG. 5. In FIG. 7A, an exemplary 100× magnification of a portion of a tunable wicking structure 700 is shown, with powder particles shown at 702. FIG. 7B shows an exemplary 250× magnification of the portion of the tunable wicking structure 700 and FIG. 7C shows an exemplary 1000× magnification of the portion of the tunable wicking structure 700. As most clearly visible in view FIG. 7C, the powder particles exhibit necking (e.g., partial bonding with adjacent particles) indicating sintering of the particles. In each of the exemplary embodiments of FIGS. 6A-C and 7A-C, the tunable wicking structures exhibit no powder fallout during cutting, as the necking of the powder particles serves to strengthen the overall structure while still allowing for the passage of liquid in gaps between the powder particles.

Figure 9:
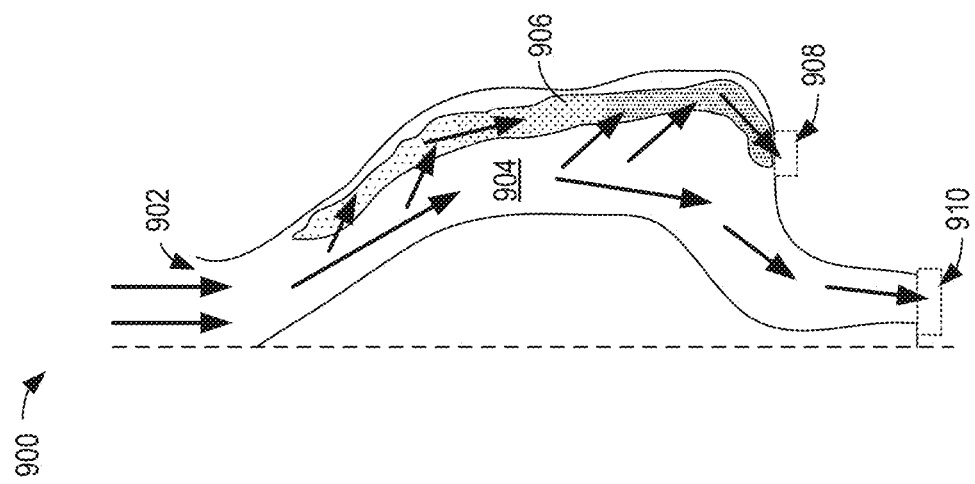
FIG. 9 schematically shows an exemplary embodiment of an air/liquid separator including a tunable wicking structure.
Figure 8:
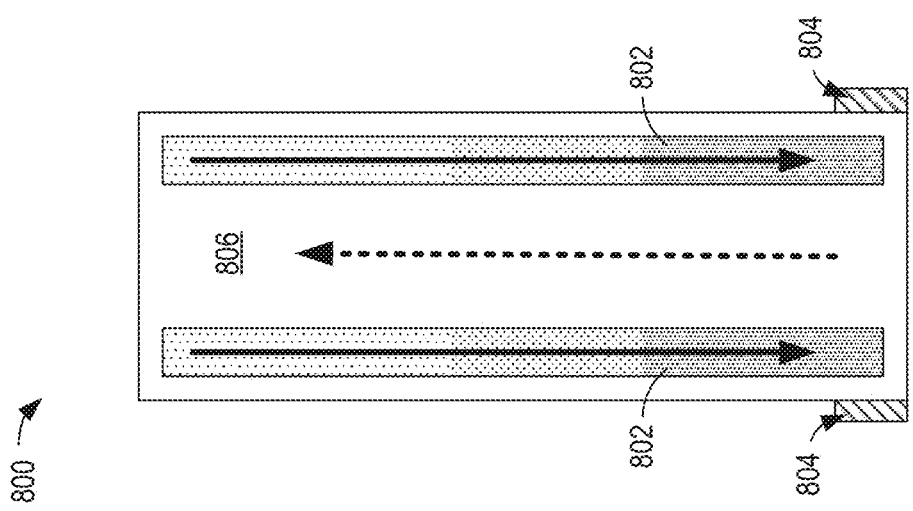
FIG. 8 schematically shows an exemplary embodiment of a heat pipe including a tunable wicking structure.
Figure 10:
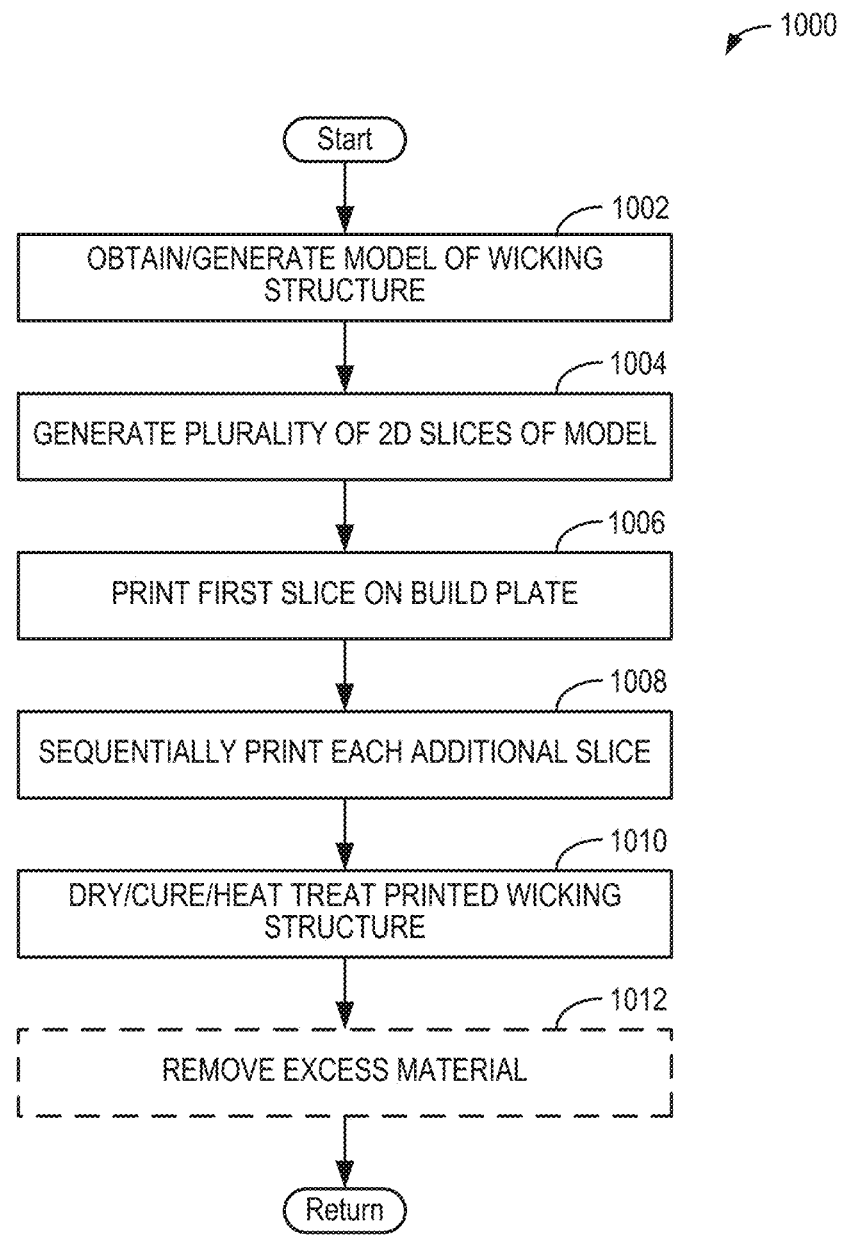
FIG. 10 shows an exemplary embodiment of a method for manufacturing a tunable wicking structure.

FIGS. 8 and 9 show exemplary embodiments of environments in which tunable wicking structures (e.g., corresponding to tunable wicking structure 200 of FIG. 2, tunable wicking structure 300 of FIG. 3 and/or any of the above-described tunable wicking structures) may be incorporated. FIG. 8 shows a cross-section of a heat pipe 800 in which liquid may be drawn downward via capillary action in a tunable wicking structure 802. A heating element 804 may be positioned at the bottom of the heat pipe and/or around a bottom periphery of the tunable wicking structure 802 in order to heat the liquid drawn by the wicking structure until the liquid is vaporized. Vaporized liquid may flow upward through a vapor chamber 806 of the heat pipe. In the example of FIG. 8, the wicking structure may have a non-uniform composition, in which pore sizes, powder particle sizes, powder sintering amount, powder density, and/or other parameters of the wicking structure may be different in different regions of the same wicking structure. For example, pore sizes may be larger and/or powder density may be denser in a top region of the tunable wicking structure relative to a bottom region of the tunable wicking structure.

FIG. 9 shows a cross-section of a portion of an air/liquid separator 900. An air/liquid mix may enter an opening 902 of a channel 904. A tunable wicking structure 906 may be positioned within the channel 904 (e.g., along a side wall of the channel), extending a portion of the length of the channel. The tunable wicking structure 906 may be configured to extract liquid from the air/liquid mix, drawing the liquid toward a liquid outlet 908 and allowing air to pass through the channel 904 toward an air outlet 910. In this way, the liquid from the air/liquid mix may be directed to a different component than the air from the air/liquid mix. The tunable wicking structure 906 may form an air barrier, keeping air moving in the channel 904 while pulling out liquid to a different receptacle. In the example of FIG. 9, the tunable wicking structure may have a non-uniform composition, in which pore sizes, powder particle sizes, powder sintering amount (e.g., amount of melting/joining of powder particles), powder density, and/or other parameters of the wicking structure may be different in different regions. For example, pore sizes may be larger and/or powder density may be denser in a top region of the wicking structure relative to a bottom region of the wicking structure in order to increase capillary action toward the liquid outlet. The wicking structure 906 of FIG. 9 may also benefit from a non-uniform size/shape that complements the shape of channel 904. Such non-uniformity may be achieved using a manufacturing method such as an additive manufacturing method, an example of which is described with respect to FIG. 10.

It is to be understood that the tunable wicking structures described herein may be used in other environments without departing from the scope of this disclosure. In another example, a wicking structure may form a tree-like structure, in which a source of liquid may be pulled from a "trunk" of the tree-like structure and distributed out to many other liquid sources and/or sinks via "branches" of the treelike structure. In this way, the amount of liquid drawn to the various sources and/or sinks may be controlled by providing different geometries and/or other wicking properties of each "branch" of the tree-like structure.

For example, each "branch" of the tree-like structure may include a wicking structure that is tuned for a particular speed, acceleration, amount, and/or other parameter of liquid delivery based on an environment in which that "branch" is located and/or a source/sink to which that "branch" is delivering the liquid. In this way, one or more "branches" may form wicking structures that are tuned to deliver liquid at a faster speed, a faster acceleration, and/or a greater amount than another "branch." In some examples, a first "branch" may include a wicking structure tuned to deliver liquid at a faster speed than a second "branch," while the second "branch" may include a wicking structure tuned to deliver a greater amount of liquid at a given time relative to the first "branch." Any of the above-described parameters of the wicking structures in the tree-like structure may be tuned (e.g., pore size, wicking structure geometry, powder particle density, etc.) in order to provide a capillary wicking capability that is tuned for an associated environment of each "branch" of the tree-like structure.

The above-described tree-like structure may be used for any of the above described tunable wicking structures. For example, the patient gas delivery system 100 of FIG. 1 may incorporate a tunable wicking structure having the above-described tree-like structure in order to deliver liquid anesthetic agent to multiple regions at different speeds, accelerations, in different amounts, etc. as described above.

FIG. 10 is a flow chart illustrating an exemplary embodiment of a method 1000 for manufacturing a wicking structure (e.g., wicking structure 200 of FIG. 2 and/or wicking structure 300 of FIG. 3). Method 1000 may be carried out at least in part by additive manufacturing, as performed by three-dimensional (3D) printing device, which may be operatively/communicatively coupled to a printer-interfacing computing device.

At 1002 a 3D model of the wicking structure is obtained and/or generated. The model of the wicking structure may be a computer aided design (CAD) file, additive manufacturing file (AMF), or other 3D modeling file. The 3D model of the wicking structure may be generated on the printer-interfacing computing device. In some examples, the 3D model may be generated entirely from operator instructions via the CAD or other program. In other embodiments, the 3D model may be generated at least in part from information received from a 3D scanner (e.g., a laser scanner) that may image a physical model of the wicking structure. The 3D model may define the dimensions of the wicking structure (e.g., a lattice defining the wicking structure), exterior and interior structures of the wicking structure (e.g., the lattice, a configuration of interior powder filling pores of the lattice, any exterior encapsulating structure, etc.), and material properties of the wicking structure, thereby fully representing, in a digital format, the final form of the wicking structure that will be produced. As appreciated by FIGS. 2 and 3, the wicking structure includes voids (e.g., empty space) and thus the 3D model of the wicking structure may include support structures, fill material, and/or other features that allow for printing over the voids. The 3D model may include a base portion of the wicking structure (e.g., from which the wicking structure extends) in order to produce a wicking structure that includes the base portion integrated with the meshwork of the wicking structure. In other embodiments, the base portion may be manufactured separately from the meshwork of the wicking structure, and thus may not be included in the 3D model. In some examples, the wicking structure may also be created entirely from the additive manufacturing machine parameters and not specifically defined in the model geometry. For example, the wick may be represented by a simplified solid cylinder 3D model and formed as a porous wick by defining the appropriate additive manufacturing machine parameters to yield a sintered or semi-sintered structure as previously described.

At 1004, a plurality of two-dimensional (2D) slices of the 3D model of the wicking structure are generated. The slices may be generated on the printer interfacing computing device and then the plurality of slices are sent to the printing device as an STL file, or the 3D model of the wicking structure may be sent to the printing device, and the printing device may slice the 3D model into the plurality of slices to generate an STL file. In doing so, the 3D model is sliced into hundreds or thousands of horizontal layers of a suitable thickness, such as a thickness in a range from 0.01 mm to 3 mm.

At 1006, the printing device prints the first slice on a build plate or other suitable base material. When the printing device prints from the STL file, the printing device creates or prints the wicking structure layer-by-layer on the build plate. The printing device reads every slice (or 2D image) from the 3D model and proceeds to create the 3D wicking structure by laying down (or printing) successive layers of material on an upper, planar surface of the build plate until the entire wicking structure is created. Each of these layers can be seen as a thinly sliced horizontal cross section of the eventually completed or printed 3D wicking structure.

The printing device may be a suitable device configured to print metal and/or other high magnetic permeability materials, such as aluminum or stainless steel. The printing device may utilize electron beam melting (EBM) technology, selective laser melting (SLM) technology, direct metal laser sintering (DMLS) technology, or other suitable metal printing technology. In some examples, the printing device may be configured to print multiple materials (e.g., the lattice and the fill powder material, or different portions of the lattice and/or fill powder material) and thus may include more than one print head.

During printing, the print head(s) is moved, in horizontal and/or vertical directions, to complete or print each layer of the 3D model, by a controlled mechanism that is operated by control software running on the printing device, e.g., a computer-aided manufacturing (CAM) software package adapted for use with the printing device. The build plate may be the component that is moved in the Z direction while the print head or lasers/electron beams may be moved in the X-Y directions to create the layers. The printed material solidifies to form a layer (and to seal together layers of the 3D wicking structure), and the print head or build plate is then moved vertically prior to starting the printing of the next layer. This process is repeated until all layers of the 3D wicking structure have been printed.

Accordingly, at 1008, each additional slice is sequentially printed. In exemplary embodiments where EBM technology is used to print the wicking structure, a sequential operation may include spreading a thin layer of powder (e.g., metal, such as titanium, or another material) on top of the build plate. In a next step of the sequential operation, an electron beam may be used to do an initial light sinter (e.g., using a first, weak electron beam or other heating mechanism) of the entire build plate in order to cause particles of the powder to lightly stick together and counteract repelling forces that are created due to charge build-up in the powder during later electron beam bombardment of the powder. The light sintering may create a powder cake. After the light sintering, a stronger, more powerful electron beam (relative to the electron beam or other heating mechanism used for the light sintering) may be used to melt each slice of the wicking structure. For each slice of the wicking structure, one or more steps of the following process may repeat: spreading a thin layer of powder on top of a last printed layer of the wicking structure, performing a light sintering of the powder (e.g., all of the thinly-spread powder), and directing an electron beam to melt a respective layer of the wicking structure. For example, the electron beam may be targeted to areas in a location of a line of a lattice structure of the wicking structure and/or areas in a location of an encapsulation structure of the wicking structure for a given slice of the wicking structure.

At 1010, the printed wicking structure is dried, cured, and/or heat treated (e.g., different heat-related processes may be performed based on a type of additive manufacturing used to build the structure). The drying/curing/heat treatment of the printed wicking structure may be performed after each layer deposition, and/or the drying/curing/heat treatment may be performed after the entire wicking structure is printed. In some examples, the drying/curing/heat treatment may include a postprocess/post-build heat treatment, where the entire wicking structure, including the powder within voids in the lattice, is heated right up to a melting point of the powder and/or just below the melting point of the powder in order to cause adjacent powder particles to exhibit necking, as shown in FIGS. 6 and 7. At 1012, any excess material (e.g., that did not bond with any adjacent powder particles during the post-process heat treatment) may optionally be removed. For example, the wicking structure may be placed into water, acid, or other solvent to at least partially dissolve the access material and/or the wicking structure may be subjected to external forces such as air blasting, vibration, etc. in order to separate excess material from the wicking structure. In another example, if support structures are printed in the voids (e.g., scaffolding-like structures or perforated structures), the support structures may be removed manually and/or with a tool.

Thus, method 1000 provides for 3D printing of a wicking structure. While method 1000 is directed to printing the entire wicking as a single component, in some examples, the 3D model of the wicking structure may include multiple 3D models, each of a different section of the wicking structure. For example, the wicking structure may be divided into a plurality of sections, such as a first section that includes the base portion and a first set of lines of material (e.g., lines of material that are intersecting, parallel, and/or otherwise positioned), a second section that includes a second set of (e.g., intersecting, parallel, etc.) lines of material, a third section that includes a third set of (e.g., intersecting, parallel, etc.) lines of material, and so forth. Each section may be printed independently, and then the sections may be stacked and fused together using a suitable mechanism. In such examples, void structures may be reduced or eliminated, which may lower the cost of manufacture.

In still further examples, the wicking structure may be manufactured using a mold. The mold may be generated by first 3D printing a model of the wicking structure in a suitable material that may be solid at room temperature but changes to liquid at a relatively low temperature that is greater than room temperature, such as wax. A plaster mold may be formed over the wax model, and after the plaster dries, the wax may be melted and drained from the mold. The mold may then be filled with molten metal. Once the metal cools, the plaster may be removed to generate the wicking structure.

Thus, the wicking structure described above with respect to FIGS. 1-9 may be manufactured using additive manufacturing technology, such as 3D printing. In an exemplary embodiment, the wicking structure described herein may be manufactured according to a computer readable medium containing computer readable instructions which, when executed on a 3D printer, cause the printer to print the wicking structure, where the wicking structure comprises a macro wicking element including a lattice structure formed by a grid of intersecting lines of material, the lattice structure including pores formed between the (e.g., intersecting, parallel, etc.) lines of material, and a micro wicking element including powder particles distributed within the pores of the lattice structure. In some examples, all or a portion of the lattice structure may be removed after printing, leaving just the powder particles forming the micro wicking structure.

In an example, a method of creating a computer readable 3D model suitable for use in additive manufacturing of a wicking structure, which may be configured to be housed in a vaporizing chamber of an anesthetic agent delivery system in some examples, is provided, wherein the wicking structure comprises a macro wicking element including a lattice structure formed by a grid or matrix of (e.g., intersecting, parallel, etc.) lines of solid material (e.g., uniform or random in size, shape, spacing, or distribution), the lattice structure including pores formed between the lines of material, and a micro wicking element including powder particles distributed within the pores of the lattice structure. In some examples the wicking structure may further include an encapsulation structure disposed around an outer surface of the macro wicking element. In some examples, the lattice structure may be configured to be removed, such that the wicking structure in a finalized form only includes the powder particles of the micro wicking element. In an example, the method includes obtaining specifications of the wicking structure. The specifications may be obtained from user input (e.g., via a 3D modeling program such as CAD) and/or from information obtained from a 3D scanner. For example, the 3D scanner may image a physical model or prototype of the wicking structure. The method further includes generating the computer readable 3D model of the wicking structure based on the obtained specifications. The 3D model may be generated using CAD or another 3D modeling program. In some examples, the method further includes sending the 3D model to a printing device. The 3D model may be converted into an STL file or other suitable format readable by the printing device. The printing device may then print the wicking structure according to the specifications set forth by the 3D model. The wicking structure may be wicking structure 200 of FIG. 2 and/or wicking structure 300 of FIG. 3, or any of the other wicking structures disclosed herein, for example.

The formation of the wicking structure in layers may also allow the wicking structure to be readily varied, with regards to geometry and configuration of powder particles and lattice structure. For example, as the layers of the wicking structure are formed, the material forms an open cell structure. A geometry of each cell of the open cell structure may be shaped by the alignment of the layers. If the layers are exactly aligned, each cell may have a same shape. In other examples, the staggering of layers may result in irregular, variable cell geometries.

A technical effect of a wicking structure formed of a plurality of powder particles is that a capillary action of the wicking structure is tunable via variation of properties of the powder particles and any associated structural components (e.g., a lattice macro structure, an encapsulating structure, etc.).

FIGS. 2-7 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A method for creating a wicking structure, comprising:
    creating, using a 3D printing technique, a macro wicking element comprising a lattice structure formed by a grid of a first material, the lattice structure comprising pores formed between the grid of first material;
    creating, using the 3D printing technique, a first micro wicking element comprising powder particles distributed within the pores of the lattice structure; and
    creating, using the 3D printing technique, a second micro wicking element by removing at least a portion of the lattice structure.

2. The method for creating the wicking structure of claim 1, wherein the grid of the first material comprises a set of parallel lines and a set of intersecting lines.

3. The method for creating the wicking structure of claim 1, wherein the first micro wicking element and the second micro wicking element are created based on a physical model obtained from a 3D scanner.

4. The method for creating the wicking structure of claim 1, wherein the first micro wicking element and the second micro wicking element are created based on one or more specifications obtained from a 3D modeling program.

5. The method for creating the wicking structure of claim 1, wherein each powder particle of the first micro wicking element is partially joined to at least one other powder particle of the wicking structure, and wherein a plurality of channels are formed between partially joined powder particles of the first micro wicking element for drawing liquid through the wicking structure via capillary action, the wicking structure having one or more tunable parameters to adjust capillary action capabilities of the wicking structure.

6. The method for creating the wicking structure of claim 1, further comprising an encapsulation structure disposed around an outer surface of the macro wicking element.

7. The method for creating the wicking structure of claim 1, wherein a porosity of the wicking structure is continuously variable along at least one dimension of the wicking structure.

8. The method for creating the wicking structure of claim 1, wherein the grid of the first material forming the lattice structure has a same material composition as the powder particles distributed within the pores of the lattice structure and wherein a size, shape, spacing, and/or distribution of the first material is uniform throughout the lattice structure.

9. The method for creating the wicking structure of claim 1, wherein the wicking structure is a wick of a vaporizer of an anesthesia machine.

10. The method for creating the wicking structure of claim 1, wherein the powder particles of the first micro wicking element are distributed uniformly throughout the pores of the lattice structure.

11. The method for creating the wicking structure of claim 1, wherein the powder particles of the first micro wicking element are distributed non-uniformly throughout the pores of the lattice structure.

* * * * *